United States Patent
Helwig et al.

(10) Patent No.: US 8,795,596 B2
(45) Date of Patent: Aug. 5, 2014

(54) GAS SENSOR WITH IMPROVED SELECTIVITY

(75) Inventors: Andreas Helwig, Munich (DE); Gerhard Muller, Grafing (DE); Jan Spannhake, Ottobrunn (DE)

(73) Assignee: EADS Deutschland GmbH, Ottobrunn (DE)

( * ) Notice: Subject to any disclaimer, the term of this patent is extended or adjusted under 35 U.S.C. 154(b) by 66 days.

(21) Appl. No.: 12/747,429

(22) PCT Filed: Nov. 27, 2008

(86) PCT No.: PCT/EP2008/010097
§ 371 (c)(1),
(2), (4) Date: Jun. 10, 2010

(87) PCT Pub. No.: WO2009/074232
PCT Pub. Date: Jun. 18, 2009

(65) Prior Publication Data
US 2010/0272611 A1    Oct. 28, 2010

(30) Foreign Application Priority Data
Dec. 10, 2007    (DE) .......................... 10 2007 059 652

(51) Int. Cl.
*G01N 15/06*    (2006.01)
(52) U.S. Cl.
USPC .......... 422/83; 422/82.01; 422/82.02; 436/43
(58) Field of Classification Search
USPC ...................... 422/83, 82.01, 82.02
See application file for complete search history.

(56) References Cited

U.S. PATENT DOCUMENTS

| | | | |
|---|---|---|---|
| 4,320,190 A | | 3/1982 | Ruedin |
| 4,352,286 A | * | 10/1982 | Nakatani et al. ............. 73/23.31 |
| 4,792,433 A | * | 12/1988 | Katsura et al. .................. 422/98 |
| 7,791,150 B1 | * | 9/2010 | Seal et al. ...................... 257/414 |
| 2004/0050207 A1 | * | 3/2004 | Wooldridge et al. ........... 75/362 |
| 2005/0045494 A1 | | 3/2005 | Huang |
| 2005/0235735 A1 | | 10/2005 | Doll et al. |
| 2006/0170015 A1 | | 8/2006 | Wienand |

FOREIGN PATENT DOCUMENTS

| | | |
|---|---|---|
| DE | 3604594 | 8/1987 |
| DE | 4401885 | 7/1995 |
| DE | 19924083 | 12/2000 |
| DE | 10200735 | 7/2003 |

(Continued)

OTHER PUBLICATIONS

C. Baratto et al. "Mixed in/Fe oxide thin films for ppb-level ozone sensing." (2003). IEEE.*

(Continued)

*Primary Examiner* — Brian J Sines
(74) *Attorney, Agent, or Firm* — McDonnell Boehnen Hulbert & Berghoff LLP

(57) ABSTRACT

The present invention relates to a gas sensor (1) for detecting gases, with at least one gas-sensitive layer which is applied to a substrate (2), wherein at least one conductor track (3) for contact-connecting the layer is also provided on the substrate (2), and wherein the conductor track (3) is formed from a doped metal oxide material with non-catalytic properties in order to avoid the conductor track (3) influencing the detection of the gas. This avoids the disadvantages of the prior art and provides contact-connection of the gas-sensitive layers which does not influence the sensitive properties when detecting the gas by means of the layer.

11 Claims, 1 Drawing Sheet

(56) References Cited

FOREIGN PATENT DOCUMENTS

| EP | 0147213 | 7/1985 |
| WO | 0244698 | 6/2002 |
| WO | 2005087986 | 9/2005 |
| WO | 2007073111 | 6/2007 |

OTHER PUBLICATIONS

O. Merdrignac-Conanec and P.T. Moseley. "Gas sensing properties of the mixed molybdenum tungsten oxide, W0.9Mo0.1O3." (published online Apr. 5, 2002). Journal of Materials Chemistry (2002) vol. 12, pp. 1779-1781.*

Helwig, Andreas et al., Temperature Characterization of Silicon Substrates for Gas Sensors by Raman Spectroscopy, ScienceDirect, Jan. 2, 2007, pp. 240-244.

Spannhake, J. et al., SnO2:Sb, A New Material for High-Temperature MEMS Heater Applications: Performance and Limitations, ScienceDirect, Jan. 13, 2007, pp. 421-428.

International Preliminary Report on Patentability for corresponding International Application No. PCT/EP2008/010097, dated Jul. 6, 2010 (17 pages).

* cited by examiner

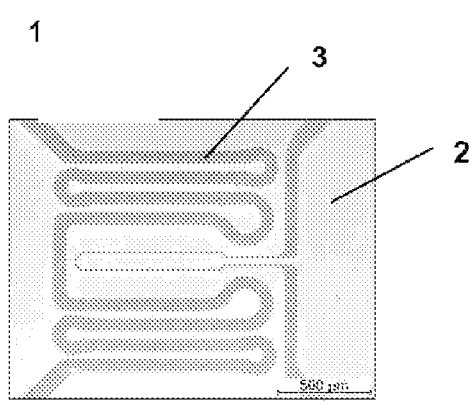
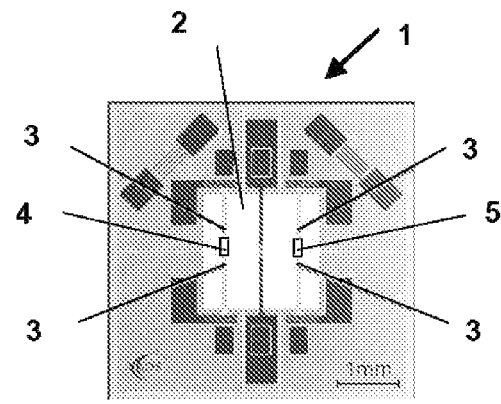
Fig. 1               Fig. 2
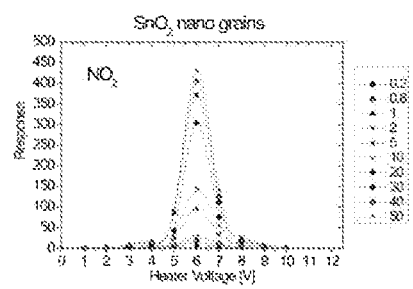
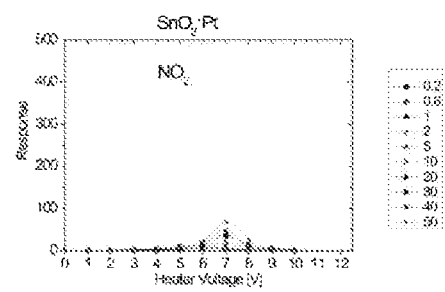
Fig. 3               Fig. 5
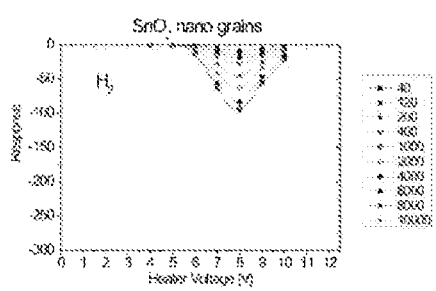
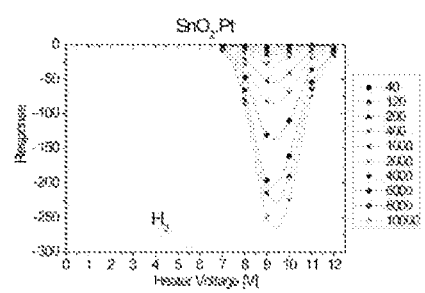
Fig. 4               Fig. 6

GAS SENSOR WITH IMPROVED SELECTIVITY

CROSS-REFERENCE TO RELATED APPLICATIONS

This application is a national stage entry of International Application No. PCT/EP2008/010097, filed on Nov. 27, 2008, which claims the benefit of the filing date of DE Application Serial No. 102007059652.0, filed Dec. 10, 2007. The entire contents of the foregoing applications are incorporated by reference herein in their entirety.

The present invention relates to a gas sensor for detecting gasses with at least one gas-sensitive layer, which is applied to a substrate, wherein at least one conductor track (PCB track) for contact-connecting the layer is also provided on the substrate.

Currently, cost-efficient thick-layer metal oxide sensors are used for the detection of various gasses and vapors. An ongoing trend towards the development in the direction of thin-layer technology is currently observed, with the aim to reduce the power consumption of these sensors. To this end, the sensitive layers of the gas sensors show a nominal layer thickness of less than 100 nm down to single nano tubes or nano clusters in the order of magnitude of a few nm. Furthermore, energy can be saved by applying these thin structures and layers onto micromechanical components. Under suited operating conditions, this results in a power consumption that is reduced by up to factor 500 compared to conventional sensors.

The gas-sensitive layers applied to the substrates are mostly operated in resistive measurement methods, so that the change of the electric resistance of the gas-sensitive layer provides information on the existence, the concentration and the type of a gas that is to be detected. A noble metal is used for contact-connecting the sensitive layers, because gas sensors mostly are operated at high temperatures.

The high reactivity towards various gasses represents a major disadvantage of metal oxide sensors. Due to the fact that these sensors react very strongly towards a plurality of gasses, an unambiguous determination of a gas and its concentration is possible, especially with a background of different temperatures, and the temperature-dependency of the gas-sensitive layers related thereto, in order to determine the gas sufficiently precise and in order to provide its concentration. However, due to temperature dependency, often a fast and precise determination of the parameters to be measured is no longer possible.

Consequently, sensor arrays comprising several sensor units that are constructed of different gas sensors are used to achieve a precise determination. The more differently the sensors react towards different gasses, the easier is the evaluation. However, the sensitivity characteristics of the single layers is adversely affected by noble metals, which themselves act as catalysts and influence the chemical reaction on the surface of the sensor. Thus, the characteristic sensitivity of the single layers is changed by the catalyst. Sensor layers, which have been laboriously grown to react distinctively, behave again nearly identical due to the effect of the catalyst. By this, the selectivity of the gas sensors is seriously compromised.

Due to the fact that these sensors react very strongly on a plurality of gasses, unambiguous determination is only possible if the sensors are operated at different temperatures. Thus, only the utilization of further means can result in a change of the sensitivity characteristics of metal oxide gas sensors. Operation at different temperatures is especially suited if sensor arrays are used, in order to exploit the different sensitivities and selectivities of the single components of the array. Different sensor units are selectively activated at different temperature levels, wherein this method is disadvantageous in that the different temperature levels have to be reached first, resulting in a reduced reaction time.

Further means relate to sensitive layers that are doped by a catalyst (platinum, gold, silver, palladium), wherein compositions like for example InSe, MoWO, InSnO are used as sensitive layers. Also, a change in the morphology of the sensitive layers, which can comprise smooth, rough, or porous surfaces, can result in enhanced selectivity. Beside the aforementioned use of the sensors at different temperatures, application of a filter layer can contribute to enhancement of selectivity.

Metal oxide gas sensors are operated in the resistive sensor mode, i.e. the change of their electric resistance serves as sensor function. For the read out of the sensor resistance, electric contacts, like the conductor tracks mentioned in the beginning, are required for contact-connecting the sensitive layers. For reasons of stability and subsequent oxidation, theses electric conductor tracks for contact-connecting are mostly made form noble metals such as platinum or gold, because metal oxide gas sensors are operated at temperatures of between 300° C. and 450° C.

From the European Patent EP 0 899 563 B1, a generic gas sensor is known that features a platinum electrode and a gold electrode, which are contact-connected with a solid electrolyte. These are in turn contact-connected with a detection means, like for example a millivoltmeter trough respective conducts, in order to pick up the measuring information. The sensor disclosed in said patent is especially suited for measurements at different temperatures, so that for example at a temperature of 300° C., there is a high sensitivity for nitrogen dioxide, at 400° C., there is a high sensitivity for nitrogen monoxide, and at 500° C., there is a high sensitivity for carbon monoxide. While this demonstrates an enhancement of selectivity by variations of the temperature, but the electrodes consisting of the noble metals likewise tend to oxidization, and can negatively affect the result of the measurement.

Consequently, with such gas sensors the problem arises that, at higher temperatures, the metals diffuse into the sensitive layer and influence its gas-sensitive properties. Already at low temperatures, the gasses react preferably and very early react on the conductor tracks and falsifies the sensor characteristic. Thinner layers react more sensitive on the doping; therefore, they are even more prone to the mentioned problems, so that the principle of measurement of different gasses with micro-mechanically constructed gas sensors is even more limited.

Thus, the problem to be solved by the present invention, to provide a gas sensor that avoids the disadvantages of the aforementioned state of the art, and that features a contact-connection of the gas-sensitive layer, which does not influence the sensitivity characteristics during the detection of gasses by the layers.

The problem is solved based on a gas sensor for the detection of various gasses according to the preamble of claim 1, in connection with the characterizing features. Advantageous developments of the invention are provided in the dependent claims.

The invention comprises a technical teaching that the conductor tracks consist of doped metal oxide material with non-catalytic properties, in order to avoid an influence of the conductor tracks on the detection of the gas.

The spirit of the present invention is to provide a material for contact-connecting the gas-sensitive layers that does not show catalytic activity and consequently does not influence the result of the measurement of the gas detection. To this end, the selection of doped metal oxide material surprisingly showed the advantage that, despite excellent electrical conductivity, a catalytic activity of the material is not detectable and that the sensor layers are not catalytically influenced by contacts with platinum, so that the selectivity of the gas-sensitive layers is significantly improved also at a constant temperature.

Advantageously, the doped metal oxide comprises a tin oxide doped with antimony (SnO2:Sb). The SnO2:Sb can be very easily produced by different methods. For example, a well suited economical production method is electron beam evaporation. If the tin oxide is doped with 5% by weight, an excellent conductivity of the doped metal oxide material as conductor track is warranted.

According to an advantageous embodiment of the gas sensor, the gas-sensitive layer for the detection of gasses is operated as resistive measuring system, in which the electric resistance of the gas-sensitive layer shows a change under the influence of a gas, by which qualitative and/or quantitative information on the type and/or presence of the gas or the gasses can be determined. The gas sensor of the present invention with conductor tracks consisting of doped metal oxide material can preferably be embodied as heated gas sensor, in which the substrate is heated, in order to operate the gas-sensitive layer for the detection of the gasses that is applied thereon, at a temperature of 100° C. to 1100° C., preferably at 200° C. to 700° C., and especially preferably at 300° C. to 450° C.

The conductor tracks can easily be structured by known processing steps like a lift-off method. After a thermal annealing step, it is fully functional. As the matter concerns an oxide, there is no danger of subsequent oxidation, so that a stability of the sensor can be achieved. Due to the use of an already oxidized material as conductor track, it is highly temperature stable and thus suited for use at over 1000° C. and, also at high temperatures, does not show catalytic activity. Concerning the lift-off method for application of the conductor tracks onto the substrate, the substrate is coated with photoresist, which subsequently is exposed to light at those positions, where the coating of the conductor tracks is removed again. Then, the substrate is coated extensively with the material of the conductor tracks, namely the doped metal oxide. During a subsequent process of removing the photoresist from the surface of the substrate, the metal oxide only remains at those positions, at which the photoresist has not been exposed to light. Resulting is a very small structure, which can be used as conductor track structure for the contact-connection of the gas-sensitive layer. This lift-off method is also suited for the application of SnO2:Sb.

Preferably, the gas-sensitive layer features a material composition of InFe, MoWO, or InSnO, which is doped with a catalyst consisting of platinum, gold, silver, and/or palladium. Further combinations of material are possible, wherein, independently from the material used for doping, an influence by the conductor tracks consisting of the doped oxide material is not detectable.

The gas-sensitive layer on the substrate can have a thickness of approximately 80 nm to 500 nm, and preferably of 100 nm. This layer thickness is only a nominal layer thickness, whereat also a further reduction of the layer thickness down to single nano tubes or nano clusters in the lower nm range is possible. The substrate of the gas sensor can be formed as micromechanical component, whereas the whole construction of the gas sensor can be translated into a chip-format, so that the gas sensor can be embodied according to the type of a lab-on-the-chip sensor.

Preferably, the gas sensor can feature a gas-sensitive layer, which is build for the measurement of NO2 and/or H2, wherein the measurement of NO2 and H2 can be performed either at the same or at different temperatures.

Further measurements that improve the invention are outlined below by means of the figures in more detail, together with the description of a preferred embodiment.

It shows:

FIG. 1 a conductor track, which consists of antimony-doped tin, on a substrate;

FIG. 2 a micromechanically manufactured gas sensor array with to layers of different sensitivity;

FIG. 3 an example of a response of a pure tin oxide sensor for nitrogen dioxide;

FIG. 4 an example of a response of the gas sensor with the gas-sensitive layer according to FIG. 3 for gaseous hydrogen;

FIG. 5 an example of a response of a gas sensor with a platinum-doped gas-sensitive tin oxide layer for nitrogen dioxide and FIG. 6 an example of a response of a gas sensor with a gas-sensitive layer according to FIG. 5 for gaseous hydrogen.

FIG. 1 depicts a conductor track 3 on a substrate 2. The conductor track 3 exhibits a doped metal oxide material, which consists of antimony-doped tin oxide (SnO2:Sb). The conductor track 3 has been applied by a lithographical lift-of method.

FIG. 2 shows a gas sensor 1 that is embodied as a micromechanically manufactured gas sensor array, which on the left side of the drawing exhibits a first gas-sensitive layer unit 4, and on the right side of the drawing exhibits a second gas-sensitive layer unit 5. The layer units 4 and 5 are connected with the respective conductor tracks 3, which according to the invention consist of antimony-doped tin oxide (SnO2:Sb). The first gas-sensitive layer unit 4 comprises a sensitive layer of pure tin oxide (SnO2). This pure SnO2 layer consists of nano grains, whereas the second gas-sensitive layer unit 5, shown on the right, also consists of a tin oxide (SnO2) layer, which additionally has been admixed with some platinum as catalyst. With this sensor array, experimental results have been determined, which are shown hereinafter exemplarily in the FIGS. 3 to 6.

FIGS. 3 and 4 show the gas response in form of a diagram, which has been measured with the nano grain-based pure tin oxide layer. Evidently, the response according to FIG. 3 for nitrogen dioxide differs considerably from the response of the gas hydrogen according to FIG. 4. The experiments have been conducted at different temperatures, wherein independently from the temperature, the response behavior can clearly be differentiated, so that different gasses are detectable with a high selectivity.

FIGS. 5 and 6 show the responses, which have been determined with the second gas-sensitive layer unit 5, in form of a diagram. Despite the doping of the tin oxide with platinum, also in this case the response behavior for the gas nitrogen dioxide and the gas hydrogen can clearly be distinguished from each other. The results demonstrate that the response behavior of both sensors varies strongly from each other. Both sensitive layers have retained their selective properties, albeit one layer has been doped with platinum. The contacting material of conductor track 3 (see FIGS. 1 and 2) does not show catalytic properties and thus does not give rise to a falsification of the selectivity profile of the single sensitive layers.

The embodiments of the invention are not limited to the preferred embodiment outlined above. In fact, a number of variants are possible that use the presented solution in otherwise different embodiments. Especially, the present invention is not limited to the embodiment of the contact-connection through conductor track 3, but any further thinkable possibility of a contact-connection of the doped metal oxide material according to the present invention can be provided.

REFERENCE NUMERALS

1 Gas sensor
2 Substrate
3 Conductor track
4 First gas-sensitive layer unit
5 Second gas-sensitive layer unit

The invention claimed is:

1. A gas sensor for the detection of gasses comprising at least one gas-sensitive layer applied on a substrate and at least one conductor track for contact-connecting the gas-sensitive layer on the substrate,
  wherein the gas-sensitive layer comprises InFe, MoWO, or InSnO doped with a catalyst of Pt, Au, Ag and/or Pd; and
  wherein the conductor track consists of an antimony-doped tin oxide ($SnO_2$:Sb) material with non-catalytic properties, and wherein the conductor track does not influence the detection of the gas.

2. The gas sensor according to claim 1, wherein the tin oxide ($SnO_2$) of the conductor track is doped with 5% by weight antimony (Sb).

3. The gas sensor according to claim 1, wherein the conductor track is applied onto the substrate through a lift-off method.

4. The gas sensor according to claim 1, wherein the gas-sensitive layer on the substrate has a thickness of approximately 80 nm to 500 nm.

5. The gas sensor according to claim 1, wherein the substrate is a micromechanical component, and wherein the gas sensor is a lab-on-the-chip sensor.

6. The gas sensor according to claim 4 wherein the gas-sensitive layer on the substrate has a thickness of approximately 100 nm.

7. A method for detecting gasses comprising
  (a) heating the substrate of the gas sensor according to claim 1 to a temperature of 100° C. to 1100° C.;
  (b) exposing the gas sensor to the gas or gasses to be detected; and
  (c) determining the existence, concentration, or the type of gasses present, or a combination thereof.

8. The method according to claim 7, wherein the substrate of the gas sensor is heated to 200° C. to 700° C.

9. The method according to claim 7, wherein the substrate of the gas sensor is heated to 300° C. to 450° C.

10. A method for detecting gasses comprising
  (a) exposing the gas sensor of claim 1 to the gas or gasses to be detected; and
  (b) determining the existence, concentration, or the type of gasses present, or a combination thereof;
  wherein the gas-sensitive layer is operated as a resistive measuring system, and
  wherein the determining of step (b) comprises measuring the electric resistance of the gas-sensitive layer.

11. The method according to claim 7 wherein the gasses to be detected are $NO_2$ and/or $H_2$, and wherein the detection of $NO_2$ and $H_2$ is performed at different temperatures.

* * * * *